United States Patent [19]

Gries et al.

[11] Patent Number: 4,869,913

[45] Date of Patent: * Sep. 26, 1989

[54] 3-SUBSTITUTED 2,4,6-TRIHALOGENATED BENZAMIDES AS SWEETENING AGENTS

[75] Inventors: Heinz Gries; Wolfgang Mützel, both of Berlin, Fed. Rep. of Germany

[73] Assignee: Schering Aktiengesellschaft, Berlin and Bergkamen, Fed. Rep. of Germany

[*] Notice: The portion of the term of this patent subsequent to Jun. 11, 2002 has been disclaimed.

[21] Appl. No.: 727,641

[22] Filed: Apr. 26, 1985

Related U.S. Application Data

[62] Division of Ser. No. 554,654, Nov. 23, 1983, Pat. No. 4,522,839, which is a division of Ser. No. 333,364, Dec. 22, 1981, Pat. No. 4,429,152.

[30] Foreign Application Priority Data

Dec. 11, 1980 [DE] Fed. Rep. of Germany ....... 3048918
Nov. 11, 1981 [DE] Fed. Rep. of Germany ....... 3145395

[51] Int. Cl.$^4$ ............................................. A23L 1/236
[52] U.S. Cl. .................................................... 426/548
[58] Field of Search ........................................ 426/548

[56] References Cited

U.S. PATENT DOCUMENTS 4,522,839 6/1985 Gries et al. ........................ 426/548

Primary Examiner—Joseph M. Golian
Attorney, Agent, or Firm—Millen, White & Zelano

[57] ABSTRACT

The 3-substituted 2,4,6-trihalogenated benzamides having the formula I

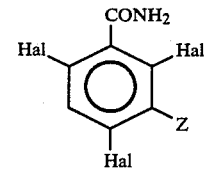

wherein
Hal is chlorine, bromine, or iodine and
Z is a carboxyl group or the group

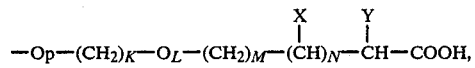

wherein P is 1 and L is 0 or 1, with the proviso that L is O when K is O;
K is 0, 2, 3 or 4;
M is 0, 1, 2 or 3;
N is 0 or 1;
X is a hydrogen atom;
Y is a hydrogen atom or a lower alkyl group of 1–4 carbon atoms, or when either M or N is other than 0, a hydroxy group, a $C_{1-6}$ alkoxy group or a $C_{1-4}$ acyloxy group, or when N is 1 and M is other than O, X and Y together represent an additional carbon-carbon bond; or P and L are each O;
K is 0, 2, 3 or 4;
M is 0, 1, 2 or 3;
N is 0 or 1;
X is a hydrogen atom;
Y is a hydrogen atom, a lower alkyl group of 1–4 carbon atoms, a hydroxy group, a $C_{1-6}$ alkoxy group, a $C_{1-6}$ acyloxy group or, when N is 1, X and Y together represent an additional carbon-carbon bond; and salts thereof with inorganic bases, exhibit an extra-ordinarily high sweetening power and are excellent substitutes for natural sweetening agents.

13 Claims, No Drawings

3-SUBSTITUTED 2,4,6-TRIHALOGENATED BENZAMIDES AS SWEETENING AGENTS

This is a division of application Ser. No. 554,654 filed 11/23/83, now U.S. Pat. No. 4,522,839, which is a division of Ser. No. 333,364 filed 12/22/81, now U.S. Pat. No. 4,429,152.

BACKGROUND OF THE INVENTION

This invention relates to 3-substituted 2,4,6-trihalogenated benzamides and their use as sweetening agents.

The so-called synthetically produced "sweeteners" with a far higher sweetening effect than cane sugar (sucrose) have been known for a long time. The most well-known representatives of this class of substances are saccharin, Dulcin, and sodium cyclamate, as well as "Aspartame" and 2-amino-4-nitro-1-phenyl-n-propyl ether ("Ultrasüss", P 4000).

Synthetic sweeteners should exhibit, besides a high degree of sweetening (low-load compound), no side effects and a very high compatibility. Furthermore, they must be able to withstand without changes the thermal stresses during the cooking or baking process. A lack of heat stability, for example, limits the range of applications of "Aspartame" to a great extent; and the objections from a health viewpoint existing against Dulcin resulted in prohibition of the use of Dulcin, for example, in the Federal Republic of Germany and in the United States of America.

Compounds of formula I wherein Hal is iodine and Z is the group

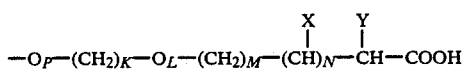

wherein
P is 1 and K, L, M are 0;
N is 0;
Y is —CH$_3$, —C$_2$H$_5$, —C$_4$H$_9$, —Phenyl; or
N is 1 or 2;
X and Y are a hydrogen atom and salts thereof with bases are disclosed in the DAS 1 568 959. They are disclosed to be suitable for use as opacifiers in cholecystography and as choleretics.

The need is great for artificial sweeteners having a stronger degree of sweetening and a further improved general compatibility, both for medical reasons (diabetics) and for dietetic reasons (reduction of calories).

SUMMARY OF THE INVENTION

The present invention relates to 3-substituted 2,4,6-trihalogenated benzamides, having the formula I

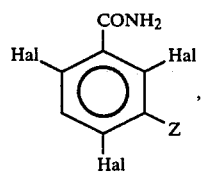

wherein
(A) Hal is a chlorine or bromine atom; and
Z is a carboxyl group, or represents the group

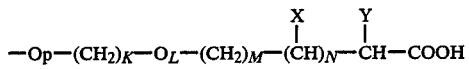

wherein
P and L are each independently 0 or 1, with the proviso that L is 0 when either P or K is 0;
K is 0, 2, 3 or 4;
M is 0, 1, 2 or 3;
N is 0 or 1;
X is a hydrogen atom;
Y is a hydrogen atom or a lower alkyl group of 1-4 carbon atoms or, when either M or N is other than 0, an optionally etherified or esterified hydroxy group, or when N is 1 and M is other than 0, X and Y together form an additional carbon-carbon bond; or wherein
(B) Hal is an iodine atom; and
Z is a carboxyl group, or represents the group

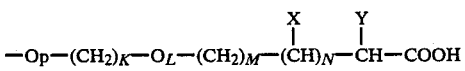

wherein
(1) P and L are each 0;
K is 0, 2, 3 or 4;
M is 0, 1, 2 or 3;
N is 0 or 1;
X is a hydrogen atom;
Y is a hydrogen atom, a lower alkyl group of 1-4 carbon atoms, or an optionally etherified or esterified hydroxy group, or when N is 1 and M is other than 0, X and Y together form an additional carbon-carbon bond; or
(2) P and L are each 1;
K is 2, 3 or 4;
M is 0, 1, 2 or 3;
N is 0 or 1;
X is a hydrogen atom; and
Y is a hydrogen atom or a lower alkyl group of 1-4 carbon atoms; or
(3) P is 1;
L is 0;
K, M and N are each 0; and
Y is a hydrogen atom; or
(4) P is 1;
L is 0;
K is 0;
M is 1 or 2;
N is 0; and
Y is a lower alkyl residue of 1-4 carbon atoms; or
(5) P is 1;
L is 0;
K is 2, 3, or 4;
M is 0, 1, 2 or 3;
N is 1;
X is a hydrogen atom; and
Y is a hydrogen atom or a lower alkyl residue of 1-4 carbon atoms;
and salts thereof with inorganic bases.

In addition, the present invention relates to sweeteners comprising a compound having the formula I

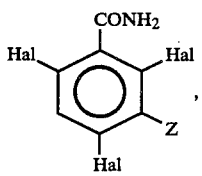

(I)

wherein
Hal is chlorine, bromine, or iodine and
Z is a carboxyl group or the group

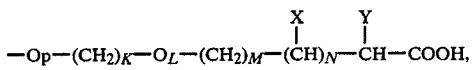

wherein
P is 1 and L is 0 or 1 with the proviso that L is 0 when K is 0;
K is 0, 2, 3 or 4;
M is 0, 1, 2 or 3;
N is 0 or 1;
X is a hydrogen atom;
Y is a hydrogen atom or a lower alkyl group of 1–4 carbon atoms, or when either M or N is other than 0, a hydroxy group, a $C_{1-6}$ alkoxy group or a $C_{1-4}$ acyloxy group; or, when N is 1 and M is other than 0, X and Y together represent an an additional carbon-carbon bond; or
P and L are 0
K is 0, 2, 3 or 4;
M is 0, 1, 2 or 3;
N is 0 or 1;
X is a hydrogen atom,
Y is a hydrogen atom, a lower alkyl group of 1–4 carbon atoms, a hydroxy group, a $C_{1-6}$ alkoxy group, a $C_{1-4}$ acyloxy group or, when N is 1, X and Y together represent an additional carbon-carbon bond;
and salts thereof with inorganic bases, in combination with a non-toxic vehicle.

In a method of use aspect, the present invention relates to the use of the foregoing compounds in place of known sweetening agents whenever such agents are used to impart a sweet taste to a composition, for medical or dietetic purposes or simply for flavoring food, drink or other composition to be ingested by mouth.

DETAILED DISCUSSION

In the compounds of formula I, suitable lower alkyl groups Y are alkyl residues of 1–4 carbon atoms, the methyl and ethyl residues being preferred. When Y is an optionally etherified hydroxy group, it is etherified with an alkyl residue of 1–6 carbon atoms, the methyl, ethyl, and n-pentyl residues being preferred.

When Y is an esterified hydroxy group, it is esterified with a $C_{1-4}$ lower carboxylic acid of 1–3 carbon atoms in the alkyl moiety, acetic acid and propionic acid being preferred.

When Z is —COOH or the group

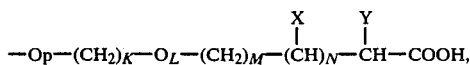

the following residues are preferred:

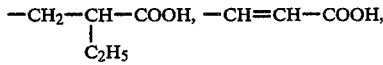

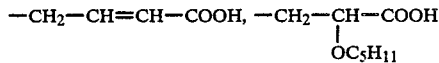

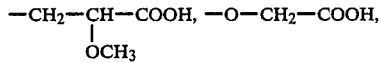

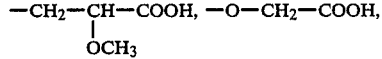

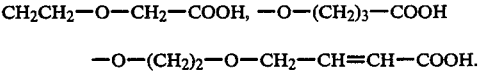

—O—(CH$_2$)$_2$—O—CH$_2$—CH=CH—COOH.

The compounds of formula I, including the novel compounds of formulae I(A) and I(B) are thermally stable, crystalline compounds and exhibit, as the acid and also in the form of their neutral salts with inorganic bases, an extraordinarily strong sweetening power. They possess the properties required of artificial sweeteners to a surprisingly high degree; for example, the sodium salt of 3-(3-carbamoyl-2,4,6-tribromophenyl)-propionic acid (A) exhibits 6000–7000 times the sweetening power of sucrose (cane sugar) and in this respect also surpasses sodium saccharin and sodium cyclamate, as borne out by the following tests.

Determination of the Sweetening Power (a) For determining the sweetening power, an aqueous 5% (g/v) (% g/v is the number of grams of agent in 100 ml of solution) sucrose solution was compared with aqueous solutions of the sodium salt of 3-(3-carbamoyl-2,4,6-tribromophenyl)propionic acid (A) as well as sodium saccharin and sodium cyclamate in up to eight concentration stages with the use of taste tests. The 0.05% solutions (concentration stage 1), from which all further solutions were prepared by dilution with water (1+1), had a pH of 5–7.

The following concentrations correspond to the 8 concentration stages tested:

| Concentration Stage No. | Concentration (mg/100 ml) | Concentration Ratio with Respect to 5% Sucrose Solution |
| --- | --- | --- |
| 1 | 50.0 | 1/100 |
| 2 | 25.0 | 1/200 |
| 3 | 12.5 | 1/400 |
| 4 | 6.25 | 1/800 |
| 5 | 3.125 | 1/1600 |
| 6 | 1.563 | 1/3200 |
| 7 | 0.781 | 1/6400 |
| 8 | 0.391 | 1/12800 |

TABLE 1

General Taste Evaluation and Degree of Sweetening of the Sodium Salt of 3-(3-Carbamoyl-2,4,6-tribromophenyl) propionic Acid (A) as Compared with Sucrose, Sodium Saccharin, and Sodium Cyclamate

| Compound | General Taste Evaluation* in Concentration Stages 1–8 | | | | | | | | Degree of Sweetening* |
|---|---|---|---|---|---|---|---|---|---|
| | 1 | 2 | 3 | 4 | 5 | 6 | 7 | 8 | |
| Sucrose | — | — | — | — | — | — | — | — | 1 |
| Sodium Saccharin | Sweet | Sweet | Slightly Sweet | Very Slightly Sweet | — | — | — | — | 400 |
| Cyclamate | Very Slightly Sweet | NT | NT | NT | — | — | — | — | <100** |
| A | Very, Very Sweet | Very Sweet | Very Sweet | Very Sweet | Very Sweet | Sweet | Sweet | Slightly Sweet | 6000–7000 |

*Average results of 3 taste tests; NT = no taste.
**As per literature: 30–70

The taste tests were conducted by three healthy volunteers; the solutions were coded by letter-number combinations and randomized so that the tester could not know which compound he or she tasted. Also the reference solution (5% sucrose) remained part of the randomizing plan initially, for the purpose of general taste characteristics of the compounds. The estimation of the degree of sweetening then took place in a second test series wherein the coding of the reference solution was revealed.

The general taste evaluation of the tested compounds and the degree of sweetening are indicated in Table 1. Since the degrees of sweetening of sodium saccharin (400) and of sodium cyclamate (70) known from the literature (see "Hager's Manual of Practical Pharmacology, 4th Ed., VII B (1977), Springer Publishers, page 426) were also determined with certainty by all three testers in a blind taste test, these results can be considered a basis for the reliability of the test results of the test compound.

(b) Another sensory test series confirmed the extraordinarily high sweetening power of the compounds of Formula I as compared with prior art compounds. In this testing series, the identification threshold values ($c_{ts}$) of compounds of this invention according to formula I, viz., 3-(3-carbamoyl-2,4,6-tribromophenyl)propionic acid (A)
3-(3-carbamoyl-2,4,6-triiodophenyl)propionic acid (E)
3-carbamoyl-2,4,6-triiodophenoxyacetic acid (F)
3-(3-carbamoyl-2,4,6-trichlorophenyl)propionic acid (G)

and of compounds of the prior art, viz., sodium saccharin, cyclamate, Dulcin, and Aspartame, were detemined and compared with the value for sucrose as the natural sweetening agent.

These sensory investigations were conducted by 5 person; all samples were encoded by a person not participating in the test. The compounds were dissolved in tap water; if necessary, the pH value was set at 6–7 with NaOH. Consecutive samples of 1 ml were consumed.

The approximate concentration values determined in a preliminary test were inserted, in the main experiment, in the middle of a dilution series. All solutions of a compound were encoded with two water samples (triangle test). The testers must indicate which of the three samples of decreasing concentration are considered to be sweet. The identification threshold value is set forth to be the lowest concentrtion range ($c_{ts}$) at which the testers still render a correct judgment.

The identification threshold values $c_{ts}$ (µmol/l) for the compounds A, E, F, and G of this invention, as well as for sodium saccharin, cyclamate, Dulcin, Aspartame, and sucrose (cane sugar) as the comparison compounds, are compiled in Table 2. If the quotient is formed from the $c_{ts}$ values of the respective compound and the $c_{ts}$ value for sucrose:

$$f_{suc} = \frac{c_{ts},\ suc}{c_{ts},\ compound},$$

then a value f is obtained, indicating how much higher the sweetening power of the tested compound is compared with sucrose. These $f_{suc}$ values are also compiled in Table 2.

TABLE 2

Identification Threshold Values ($c_{ts}$) of Several Sweeteners

| Compound | MW | (µmol/l) | $f_{suc,\ mol}$ ($c_{ts}$) |
|---|---|---|---|
| G | 296.54 | 2.5–4.0 | 3385 |
| A | 451.89 | 0.6–1.4 | 11000 |
| E | 570.88 | 1.0–2.0 | 7333 |
| F | 584.92 | 15–25 | 550 |
| Sodium Saccharin | 183.19 | 15–30 | 489 |
| Cyclamate | 201.22 | 1000–3000 | 5.5 |
| Dulcin | 180.2 | 15–30 | 489 |
| Aspartame | 294.3 | 20–60 | 275 |
| Sucrose | 342.3 | 10000–12000 | 1 |

It can be seen from Table 2 that the compounds A, E, F, and G of this invention possess a greater sweetening power (f ≧550) than sodium saccharin (f=489), the strongest artificial sweetener known heretofore.

The compounds of formula I according to this invention moreover exhibit an excellent general compatibility. As can be seen from Table 3, with intraperitoneal injection in mice, the sodium salt of 3-(3-carbamoyl-2,4,6tribromophenyl)propionic acid (A) shows approximately the same good compatibility as sodium saccharin.

TABLE 3

| Test Compound | Dose (g/kg BW) | Finding (Number of Dead Animals/Number of Animals Utilized) |
|---|---|---|
| A | 3.0 | 2/10 |
| | 6.0 | 6/10 |
| | 9.0 | 10/10 |
| Sodium Saccharin | 3.0 | 0/10 |
| | 6.0 | 5/10 |
| | 10.0 | 9/10 |

According to these results, the LD$_{50}$ after a one-time intraperitoneal administration of sodium saccharin and of compound A is approximately at 6.0 g/kg body weight. The LD50 found for sodium saccharin agrees with the LD$_{50}$ after i.p. administration to mice reported previously by Taylor, et al., in 37 Toxicological Studies with Sodium Cyclamate and Saccharin" *Fd. Cosmet. Toxicol.*, 6, 313–327 (1968). Insofar as its practical utilization as a substitute compound for sodium saccharin, this good compatibility of compound A, which here can be estimated only roughly, must be considered to be very advantageous since it will probably be possible to make do with one-tenth of the sodium saccharin dose due to the very high sweetening power of the sweeteners of formula I according to this invention.

The compounds of formula I are utilized as acids as well as in the form of their salts with inorganic bases, to serve as sweeteners.

Suitable such salts include, e.g., sodium, potassium and calcium salts, formed by neutralizing the acid form of compounds having formula I with inorganic bases such as, e.g., sodium hydroxide, sodium carbonate, potassium hydroxide, potassium carbonate, calcium hydroxide, calcium carbonate, and the like.

Compounds having formula I, wherein Hal is an iodine atom are also useful as radio-opaque agents.

The invention also concerns sweeteners comprising a compound of formula I as sweetening agents and utilized in the form of tablets or as a solution. The sweeteners are produced according to methods known to those skilled in the art. The compound of formula I is combined with a non-toxic vehicle to produce the sweeteners. For producing the tablets, the procedure is suitably such that a water-soluble auxiliary agent and a water-soluble lubricant (emulsifier) are combined with at least one compound of formula I and pressed into tablets in a tabletting press. Advantageously, the weight of one table is 40 mg, preferably 50 mg, the content of active agent then being 5 mg to 15 mg, preferably 10 mg, and the content of emulsifier being 0.2 mg to 0.3 mg:

Water-soluble auxiliary agents are compounds which are also tolerated by diabetics, e.g., fructose, lactose, mannitol, or sorbitol, wherein fructose and lactose are preferred. Lubricants (emulsifiers) are preferably non-ionic emulsifiers, e.g., polyoxyethylene-polyoxypropylene polymers, polyoxyethylene glycols, ascorbyl palmitate, polyoxyethylated compounds, such as polyoxyethylene stearates or polyoxyethylene fatty alcohols, or the ethers thereof, wherin polyoxyethylene-polyoxypropylene polymer having a molecular weight of 6800 and polyehtylene glycols having a molecular weight of 6000 are preferred.

For producing a sweetener solution, at least one compound of formula I is dissolved in distilled water; optionally, the solution is additionally combined with a material acting as a thickener in order to facilitate handling and dosing. The concentration of compounds of formula I in the solution is suitably 10 g to 20 g per liter, 15 g per liter being preferred. Suitable thickeners include, e.g., gelatin, hydroxypropylcellulose, carboxymethylcellulose, water-soluble cellulose ethers, 0.1% to 0.8% being contained in the solution. Gelatin and hydroxypropylcellulose are preferred.

Sweeteners of the invention are useful as substitutes for natural sweeteners, such as sucrose or glucose, especially for persons who must restrict their sugar consumption for either medical reasons, e.g., diabetics, or for dietetic reasons, e.g., to reduce caloric intake. Such persons, or animals, will advantageously substitute the sweeteners of the invention for at least a portion of the sugar or caloric sweeteners in their diet. For this purpose, they will consume an ingestible composition comprising as a sweetening agent an effective sweetening amount of a compound of formula I.

The compounds of formula I may be produced by a process wherein (a) a compound of formula II

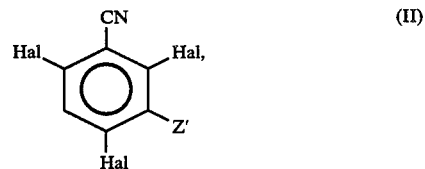

wherein

Hal is a chlorine, bromine or iodine atom and
Z' is the group —COOH, —COOR$^1$, or

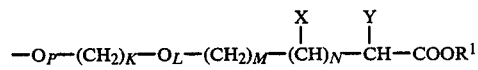

wherein R$^1$ is a hydrogen atom or a lower alkyl residue of 1–4 carbon atoms, and P, K, L, M, N, X and Y are as defined above for formula I, is partially hydrolyzed to the benzamide conventionally by reaction with an alkali; or (b) for preparing compounds of the formula I(A) wherein P is 1, a compound of the formula III

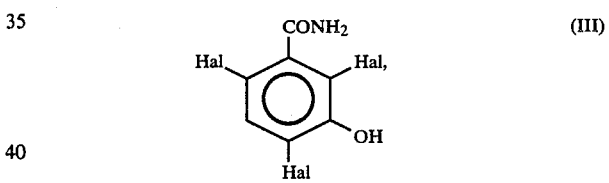

wherein Hal is a chlorine or bromine atom, is converted to its alkali metal phenolate and reacted, in a manner known per se, with a compound of Formula IV

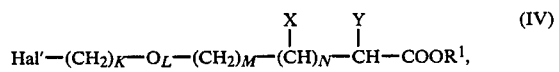

wherein

Hal' is a chlorine or bromine atom,
R$^1$ is a lower alkyl residue of 1–4 carbon atoms, and
K, L, M, N, X and Y are as defined for formula I(A); or (c) a compound of Formula III, wherein Hal is an iodine atom, is converted to its alkali phenolate and conventionally reacted with a compound of Formula IV wherein Hal' and R$^1$ are as defined above, and K, L, M, N, X and Y are as defined for formula I(B) and subsequently, if desired, any present carboxylic acid lower alkyl esters are saponified and/or salts are produced by reaction with inorganic bases.

Suitable lower alkyl groups R$^1$ are alkyl residues of 1–4 carbon atoms, the methyl and ethyl residues being preferred.

The partial hydrolysis of the nitrile group to the carbamoyl group, required to produce the compounds of formula I according to this invention, is effected by using methods known to those skilled in the art. The term "partial hydrolysis" is meant to denote hydrolysis of the nitrile to an amide function, but not further hydrolysis to the carboxyl group, which could be considered complete hydrolysis. Thus, the nitrile group can be converted into the amide, for example, by dissolving the nitrile precursor in concentrated mineral acids, such as hydrochloric acid, sulfuric acid, or phosphoric acid and conducting the hydrolysis at temperatures of about room temperature to 100° C., preferably at 50°–100° C. The nitrile group can, however, also be partially hydrolyzed in an alkaline medium by dissolving or suspending the starting compound in an aqueous alkali metal hydroxide and hydrolyzing the mixture at a temperature of about room temperature to 100° C., preferably at 40°–80° C.

The starting compounds of formula II required for process pathway (a) are, in part, known or can be prepared using methods known to persons skilled in the art. Thus, for example, compounds of formula II, wherein Hal is an iodine atom; Z' is either —COOH or the group

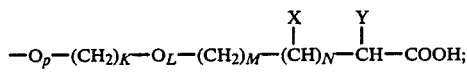

and P and L are 0, are described in German Unexamined Laid-Open Application DOS 2,831,496 together with processes for the preparation thereof.

Compounds of formula II, wherein Hal is a bromine or chlorine atom; Z' is either —COOH or the group

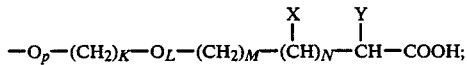

and P and L are 0, can be produced, for example, by reacting an aniline derivative of formula V with a halogenating agent, e.g., sulfuryl chloride, in a suitable solvent such as, for example, benzene, toluene, or ethylene chloride, or with molecular halogen in a suitable solvent such as, for example, glacial acetic acid or ethylene chloride, to obtain the trihalogenated aniline of formula VI

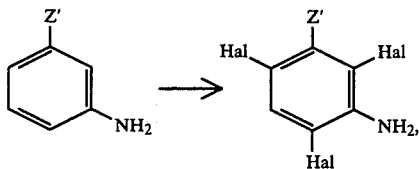

wherein
Hal is a bromine or chlorine atom;
Z' is either —COOH or the group

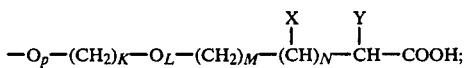

and P and L are 0.

The resultant trihalogenated aniline derivatives of formula VI are converted, in accordance with the process described in DOS 2,831,496, in a Sandmeyer reaction, by diazotization and subsequent reaction with cyanides into the benzonitriles of general formula II wherein Z' is either —COOH or the group

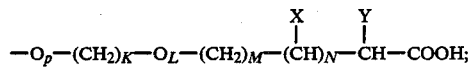

and P and L are 0.

The following directions for the preparation of 3-(3-cyano-2,4,6-trichlorophenyl)propionic acid and for the corresponding 2,4,6-tribromo compound are set forth to explain the individual reaction steps:

3-(3-Cyano-2,4,6-trichlorophenyl)propionic Acid:

30 g of 3-(3-aminophenyl)propionic acid is suspended in 2 l of benzene, 220 ml of sulfuryl chloride is added dropwise thereto, and the batch is heated for 90 minutes to reflux. The product is filtered off under heating from a small amount of undissolved starting material, and the filtrate is concentrated to dryness. The residue is combined with 900 ml of water and heated under agitation on a steam bath for 1 hour. Then, 366 ml of a 25% sodium carbonate solution is added in incremental portions to the reaction mixture and the latter heated again under stirring on a steam bath for 30 minutes. After clarifying the solution over active carbon, a pH of 2 is set under agitation and cooling by adding concentrated hydrochloric acid. After stirring for several hours in an ice bath, the precipitate is vacuum-filtered, washed with water, and dried at 50° C., thus obtaining 33 g (68% of theory) of 3-(3-amino-2,4,6-trichlorophenyl)propionic acid as a white powder, mp 145° C.

7 g of sodium nitrite is introduced under agitation at +5° C. into 84 ml of concentrated sulfuric acid. The mixture is stirred for another 10 minutes and then heated to 70° C. to obtain a clear solution. After cooling to 5° C., 42 ml of glacial acetic acid is added thereto under ice bath cooling. The, 21.5 g of 3-(3-amino-2,4,6-trichlorophenyl)propionic acid is added in incremental portions at between 0° C. and +5° C., and the mixture is stirred for 2 hours at 5° C. The mixture is poured on 200 g of ice and thereafter, under agitation, is introduced into a solution of 35.4 g of copper(I) cyanide and 66.8 g of potassium cyanide in 900 ml of semi-concentrated ammonia; during this step, nitrogen is liberated. After stirring overnight at room temperature, 800 ml of ethyl acetate is added and the mixture is brought to pH 1 by dropwise addition of concentrated hydrochloric acid. After separating the precipitated inorganic salts by vacuum-filtering, the ethyl acetate phase is removed, washed twice with respectively 300 ml of water, and evaporated to dryness after drying over sodium sulfate. Recrystallization from seven times the amount of toluene yields 16 g (72% of theory) of 3-(3-cyano-2,4,6-trichlorophenyl)propionic acid as a white powder, mp 127°–129° C.

The following compounds are produced analogously:
3-cyano-2,4,6-trichlorophenylacetic acid (mp 182°–184° C.) with a total yield of 49% of theory, from 3-aminophenylacetic acid (mp 152° C.) via the intermediate 3-amino-2,4,6-trichlorophenylacetic acid (mp 206° C.) and 3-cyano-2,4,6-trichlorobenzoic acid (mp 138°–142° C.) with a total yield of 42% of theory, from 3-aminobenzoic acid (mp 178° C.) via the intermediate 3-amino-2,4,6-trichlorobenzoic acid (mp 159°–161° C.).

3-(3-Cyano-2,4,6-tribromophenyl)propionic Acid:

32.7 g of 3-(3-aminophenyl)propionic acid is suspended in 1 liter of water and dissolved by adding concentrated ammonium hydroxide, 160 ml of glacial acetic acid is added thereto, and then a solution of 36 ml of bromine in 160 ml of glacial acetic acid is added within 2 hours at room temperature under thorough agitation. the mixture is stirred for 2 hours, the precipitate is vacuum-filtered, washed with water, dried at 50° C., and recrystallized from four times the amount of ethyl acetate with active-carbon treatment, thus obtaining 63 g (78% of theory) of 3-(3-amino-2,4,6-tribromophenyl)-propionic acid as a white powder, mp 195°–197° C.

3.5 g of sodium nitrite is introduced at 5° C. under agitation into 42 ml of concentrated sulfuric acid, stirred for 10 minutes, and then heated to 70° C. until a clear solution is obtained. After cooling to 5° C., 21 ml of glacial acetic acid is added under cooling in an ice bath. Then 16 g of 3-(3-amino-2,4,6-tribromophenyl)propionic acid is introduced in incremental portions between 0° C. and 5° C., and the mixture is agitated for 2 hours at 5° C. The mixture is poured on 200 g of ice and then under agitation is introduced into a solution of 18 g of copper(I) cyanide and 33.5 g of potassium cyanide in 450 ml of semiconcentrated ammonia, thus liberating nitrogen. The solution is saturated with sodium chloride and stirred overnight under water cooling. The thus-separated ammonium salt is vacuum-filtered and dissolved in the moist state in 200 ml of water. The solution is brought to pH 1 after treatment with activated carbon, by the addition of concentrated hydrochloric acid. After stirring for several hours in an ice bath, the precipitate is vacuum-filtered, washed with water, and dried at 50° C., thus producing 13 g (83% of theory) of 3-(3-cyano-2,4,6-tribromophenyl)propionic acid as a white powder, mp 164°–166° C.

Analogously, the following compounds are prepared:
3-cyano-2,4,6-tribromophenylacetic acid (mp 233° C.) with a yield of 62% of theory, from 3-aminophenylacetic acid (mp 152° C.) via the intermediate 3-amino-2,4,6-tribromophenylacetic acid (mp 229°–231° C.) and 3-cyano-2,4,6-tribromobenzoic acid (mp 168° C.) with a yield of 75% of theory, from 3-aminobenzoic acid (mp 178° C.) via the intermediate 3-amino-2,4,6-tribromobenzoic acid (mp 180° C.).

For the production of compounds of general formula I, wherein P is 1, according to process pathway (a), the starting compounds are advantageously the corresponding 2,4,6-trihalogen-3-hydroxybenzonitriles, the tribromo and trichloro compounds being known. The heretofore unknown 2,4,6-triiodo-3-hydroxybenzonitrile can be readily prepared by iodination of 3-hydroxybenzonitrile as follows:

To a solution of 11.9 g (100 millimoles) of 3-hydroxybenzonitrile in 130 ml of glacial acetic acid is added over 2 hours a solution of 53 g (327 mmol) of iodine monochloride in 80 ml of glacial acetic acid. After 30 minutes, 400 ml of water is added dropwise thereto, and the mixture is stirred for 24 hours at 35° C. Subsequently, the mixture is cooled to room temperature and the excess iodine monochloride is decomposed by adding solid sodium bisulfite. The iodination product, removed by vacuum-filtering, is washed with sodium bisulfite solution, then with water to render the product neutral, and dried. Yield: 31 g (62% of theory) of 3-hydroxy-2,4,6-triiodobenzonitrile as a creamcolored powder, mp 242–245° C. (decomposition).

The 2,4,6-trihalo-3-hydroxybenzonitriles are then alkylated with the desired halogen compound of formula IV according to the conventional processes described hereinabove, which are well known in the art.

The following illustrative preparation will further exemplify the alkylation reaction:

3-Cyano-2,4,6-trichlorophenoxyacetic acid methyl ester 22.5 (0.1 mol) of 3-hydroxy-2,4,6-trichlorobenzonitrile are dissolved in 240 ml of methanol with the addition of 2.3 g (0.1 mol) of metallic sodium. To the resultant suspension of the sodium salt is added 12.15 ml (0.11 mol) of ethyl bromoacetate, and the reaction mixture is heated to reflux until solution is complete. After filtration over active carbon, the solution is cooled and stirred for several hours in an ice bath. The resultant crystalline precipitate is vacuum-filtered, washed with a little icecold methanol and dried at 50° C., to produce 19 g (64.5% of theory) of 3-cyano-2,4,6-trichlorophenoxyacetic acid methyl ester as a white powder 110°–112° C.

The halogen compounds of formula IV required for the alkylation of the above-described 2,4,6-trihalo-3-hydroxybenzonitriles as well as of the compounds of formula III of process pathway (b), described below, are mostly known or can be produced according to conventional processes as described, for example, in European Pat. No. 0001740.

The compounds of formula I, wherein P is 1, are prepared by following process pathway (b), by methods known to persons skilled in the art. Thus, for example, the phenol of formula III, dissolved in a mono- or polyhydric alcohol, such as methanol, ethanol, glycol, glycerin, but also diethylene glycol or dimethylformamide, can be converted with the equivalent amount of alkali metal alcoholate into the alkali metal phenolate and by heating, optionally to boiling, with somewhat more than the equivalent quantity of alkyl halide of formula IV, can be converted into the phenol ether, as known to those skilled in the art. Preferably, when conducting process pathway (b), sodium alcoholate is used as the base; methanol or ethanol is used as the solvent, and the corresponding chloride or bromide is used as the alkyl halide of formula IV.

However, it is also possible to react the phenol of formula III under boiling in a suitable solvent, e.g., acetone, with an excess of alkali metal carbonate, preferably potassium carbonate, and the desired alkyl halide of formula IV, which is used in about 10% excess; in this connection, addition of alkali metal iodide facilitates the reaction. If higher reaction temperatures are required, higher-boiling ketones can be used, such as methyl ethyl ketone or cyclohexanone. Preferred alkyl halides of formula IV are the chloride or the bromide.

The starting materials of formula III required for conducting process pathway (b)

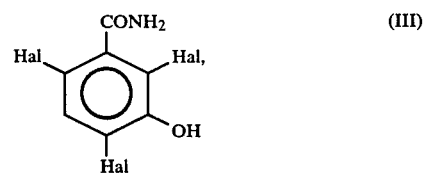

are known with HAL =iodine, e.g., as disclosed in G. Tilly, *Chim. Ther.*, 2(1) 57-65 (1967), or can be prepared from 3-hydroxybenzamide by halogenation according to processes known to person skilled in the art in accordance with the following illustrative directions:

3-Hydroxy-2,4,6-trichlorobenzamide 25 g (180 mmol) of 3-hydroxybenzamide is dissolved in 500 ml of glacial acetic acid. At 35° C., 26 g of chlorine is then introduced into the solution and the latter stirred at 60° C. for 4 hours. After evaporation under vacuum to dryness, the residue is combined with 150 ml of water, stirred for several hours in an ice bath, and the precipitate is vacuum-filtered. After washing with water and drying, 34 g (80% of theory) of 3-hydroxy-2,4,6-trichlorobenzamide is obtained as a white powder, mp 204°-206° C.

3-Hydroxy-2,4,6-tribromobenzamide 40 g (0.29 mol of 3-hydroxybenzamide is suspended in 1.5 l of water and dissolved by adding concentrated ammonia. The solution is then brought of pH 5 by adding glacial acetic acid, and a solution of 79.9 g (1 mol) of bromine in 200 ml of glacial acetic acid is added thereto dropwise over two hours at room temperature. The mixture is stirred for two hours, the thus-formed precipitate is vacuum-filtered, washed with 500 ml of a 10% sodium bisulfite solution and then with water, and dried at 60° C., yielding 103 g (95% of theory) of 3-hydroxy-2,4,6-tribromobenzamide as a yellowish-white powder, mp 225°-226° C. (decomposition).

If it proves to be necessary during the course of the process of this invention to saponify any produced carboxylic acid lower alkyl esters, this is effected by means of methods known to those skilled in the art. Thus, it is possible to suspend the ester in water, to add an excess of alkali metal hydroxide, and to conduct the saponification at a temperature of 20°-80° C., preferably 50°-70° C. Subsequently the solution is purified by filtration, preferably over active carbon, and mineral acid is added until an acidic reaction is obtained, whereupon the acid of formula I can be isolated. To prepare the alkali metal salts, the acid of formula I is suspended in a suitable solvent, e.g., in a mixture of ethanol or methanol with water, and converted with the equivalent amount of dilute alkali metal hydroxide, preferably sodium or potassium hydroxide, into the alkali metal salt; the solution is purified by filtration, and the salt is isolated.

The examples set forth below will explain the invention in greater detail.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

3-(3-Carbamoyl-2,4,6-trichlorophenyl)propionic Acid 16 g of 3-(3-cyano-2,4,6-trichlorophenyl)propionic acid is dissolved in a solution of 5 g of solution of caustic soda in 80 ml of water. The mixture is maintained at 60° C. for 3 hours, filtered over active carbon, and the filtrate is brought to pH 1 under cooling by the addition of concentrated hydrochloric acid under agitation. After several hours of stirring, the precipitate is vacuum-filtered, washed with water, and dried at 50° C. Recrystallization from five times the amount of toluene yields 15.5 g (90% of theory) of 3-(3-carbamoyl-2,4,6-trichlorphenyl)propionic acid as a white powder, mp 196°-198° C.

EXAMPLE 2

3-Carbamoyl-2,4,6-trichlorophenylacetic Acid

As described in Example 1, 3-cyano-2,4,6-trichlorophenylacetic acid yields, with 88% of theory, 3-carbamoyl-2,4,6-trichlorophenylacetic acid, mp 211° C.

EXAMPLE 3

2,4,6-Trichloroisophthalamic Acid

As described in Example, 1, 3-cyano-2,4,6-trichlorobenzoic acid results, with a yield of 88% of theory, in 2,4,6-trichloroisophthalamic acid, mp 280° C.

EXAMPLE 4

3(3-Carbamoyl-2,4,6-tribromophenyl)propionic Acid

A. Alkaline Saponification:

13 g of 3-(3-cyano-2,4,6-tribromophenyl)propionic acid is introduced into a solution of 3.2 g of caustic soda in 64 ml of water. The solution is then stirred for 3 hours at 60° C., filtered repeatedly over active carbon to decolorize, and subsequently the filtrate is brought to pH 1 by the addition of concentrated hydrochloric acid. The precipitate is vacuum-filtered, washed with water, and dried at 50° C., thus obtaining 16 g (95% of theory) of 3-(3-carbamoyl-2,4,6-tribromophenyl)propionic acid as a white powder, mp 197° C.

B. Acidic Hydrolysis:

13 g of 3-(3-cyano-2,4,6-tribromophenyl)propionic acid is suspended in 50 ml of concentrated sulfuric acid and heated initially to 60° C. for 30 minutes and thereafter to 95° C. for 2 hours. The solution is then poured on 300 g of ice and agitated for 3 hours in an ice bath. The thus-precipitated product is vacuum-filtered, washed with ice water, and dried at 50° C. under vacuum. Yield: 14 g of 3-(3-carbamoyl-2,4,6-tribromophenyl)propionic acid with 90% of theory, mp 197° C.

EXAMPLE 5

3-Carbamoyl-2,4,6-tribromophenylacetic Acid

As described in Example 4, 3-cyano-2,4,6-tribromophenylacetic acid is used to obtain, with 90% of theory, 3-carbamoyl-2,4,6-tribromophenylacetic acid, mp 245° C.

EXAMPLE 6

2,4,6-Tribromoisophthalamic Acid

As described in Example 4, 3-cyano-2,4,6-tribromobenzoic acid yields, with 92% of theory, 2,4,6-tribromoisophthalamic acid, mp>280° C.

EXAMPLE 7

3(3-Carbamoyl-2,4,6-triiodophenyl)propionic Acid 30 g of 3-(3-cyano-2,4,6-triiodophenyl)propionic acid is introduced into a solution of 8 g of caustic soda in 100 ml of water. The solution is then maintained for 3 hours at 60° C., decolorized by repeated treatment with active carbon, and brought to pH 1 by adding concentrated hydrochloric acid. After several hours of agitation in an ice bath, the precipitate is vacuum-filtered, washed with water, and dried at 50° C. Yield: 29 g (94% of theory) of 3-(3-carbamoyl-2,4,6-triiodophenyl)propionic acid as a white powder, mp>280° C.

Analogously, the following compounds are obtained from the corresponding nitriles:
2,4,6-triiodoisophthalamic acid
3-(3-carbamoyl-2,4,6-triiodophenyl)-2-ethylpropionic acid
3-(3-carbamoyl-2,4,6-triiodophenyl)acrylic acid
3-(3-carbamoyl-2,4,6-triiodophenyl)-2-n-amyloxypropionic acid
5-(3-carbamoyl-2,4,6-triiodophenyl)pentanoic acid.

EXAMPLE 8

3-Carbamoyl-2,4,6-tribromophenoxyacetic Acid 35.5 g (95 mmol) of 3-hydroxy-2,4,6-tribromobenzamide is suspended in 150 ml of methanol and dissolved by adding 2.18 g (95 mmol) of sodium. The mixture is combined with 17.5 g (104 mmol) of ethyl bromoacetate and maintained under reflux for three hours. After several hours of agitation, the crystallized product is vacuum-filtered, washed with a small amount of ice-cold methanol, and dried at 60° C., thus obtaining 37.2 g (88% of theory) of 3-carbamoyl-2,4,6tribromophenoxyacetic acid methyl ester, mp 231°–233° C.

30 g (67 mmol) of 3-carbamoyl-2,4,6-tribromophenoxyacetic acid methyl ester is suspended in 300 ml of water, the suspension if heated to 60° C., and the ester is saponified by the dropwise addition of 25 ml of concentrated sodium hydroxide solution. The solution is filtered over active carbon and brought to pH 1 by adding concentrated hydrochloric acid dropwise under ice bath cooling. After several hours of agitation, the thus-formed sediment if vacuum-filtered, washed with water, and dried at 60° C. Yield: 28 g (97% of theory) of 3-carbamoyl-2,4,6-tribromophenoxyacetic acid as a white powder, mp 271°–272° C. (decomposition).

EXAMPLE 9

4-(3-Carbamoyl-2,4,6-tribromophenoxy)butyric Acid 25 g (66.9 mmol) of 3-hydroxy-2,4,6-tribromobenzamide is suspended in 100 ml of methanol and dissolved by adding 1.54 g (66.9 mmol) of sodium. After adding 14 g (73 mmol) of the ethyl ester of 4-bromobutyric acid, the mixture is maintained under reflux for 70 hours, and then the solution is evaporated to dryness and the residue extracted under boiling with 250 ml of ether. After several hours of stirring in an ice bath, the precipitate is vacuum-filtered, washed with ether, and dried at room temperature, thus obtaining 19 g (58% of theory) of 4-(3-carbamoyl-2,4,6-tribromophenoxy)-butyric acid ethyl ester as a white powder, mp 138°–140° C.

18 g (36.9mmol) of 4-(3-carbamoyl-2,4,6-tribromophenoxy)butyric acid ethyl ester is suspended in 180 ml of water and, after adding 10 ml of concentrated sodium hydroxide solution, saponified at 60° C. within three hours. The solution is filtered over active carbon and brought to pH 1 by the dropwise addition of concentrated hydrochloric acid. After several hours of agitation in an ice bath, the resultant precipitate is vacuum-filtered, washed with water, and dried at 60° C. Yield: 15 g (88% of theory) of 4-(3-carbamoyl-2,4,6-tribromophenoxy)butyric acid as a white powder, mp 193°–194° C.

EXAMPLE 10

5-(3-Carbamoyl-2,4,6-trichlorophenoxy)-3-oxapentanoic Acid Sodium Salt 2.3 g (10 mmol) of sodium is dissolved in 200 ml of ethanol and then 24 g (10 mmol) of 3-hydroxy-2,4,6-trichlorobenzamide, 16.7 g (10 mmol) of 5-chloro-3-oxapentanoic acid ethyl ester, and 0.3 g of potassium iodide are added to the reaction mixture, and the latter is maintained under reflux for 24 hours. After adding 1 liter of water, the mixture is agitated for 30 minutes in an ice bath, the resultant precipitate is vacuum-filtered and washed with water. Subsequently the moist ethyl ester of 5-(3-carbamoyl-2,4,6-trichlorphenoxy)-3-oxapentanoic acid is suspended in 250 ml of water and, after adding 40 ml of semiconcentrated sodium hydroxide solution, saponified at 60° C. within three hours. The solution is filtered over active carbon, cooled to room temperature, and brought to pH 1 by adding concentrated hydrochloric acid. After several hours of stirring in an ice bath, the thus-separated 5-(3-carbamoyl-2,4,6-trichlorophenoxy)-3-oxapentanoic acid is vacuum-filtered, washed neutral with water, and then dissolved in 300 ml of a mixture of equal parts of ethanol and water after neutralization by the addition of 2N sodium hydroxide solution. The solution is treated with active carbon and then concentrated to dryness under vacuum, thus obtaining 29.8 g (82% of theory) of the sodium salt of 5-(3-carbamoyl-2,4,6-trichlorophenoxy)-3-oxapentanoic acid.

EXAMPLE 11

3-Carbamoyl-2,4,6-trichlorophenoxyacetic Acid 16 g (66.9 mmol) of 3-hydroxy-2,4,6-trichlorobenzamide is suspended in 100 ml of methanol and dissolved by adding 1.54 g (66.9 mmol) of sodium. After the addition of 16.8 g (66.9 mmol) of bromoacetic acid ethyl ester, the mixture is maintained under reflux until the reaction is complete (TLC control). The product is then concentrated to dryness under vacuum and the resultant 3-carbamoyl-2,4,6-trichlorophenoxyacetic acid methyl ester is suspended in 100 ml of water. The mixture is combined with 20 ml of concentrated sodium hydroxide solution and maintained for 3 hours at 60° C. for saponifying. The solution is filtered over active carbon, brought to pH 2 by adding concentrated hydrochloric acid, and the precipitate is vacuum-filtered after several hours of stirring in an ice bath. After washing with water and drying, 16.8 g (84% of theory) of 3-carbamoyl-2,4,6-trichlorophenoxyacetic acid is obtained as a white powder, mp 261°–262° C.

EXAMPLE 12

4-(3-Carbamoyl-2,4,6-trichlorophenoxy)butyric Acid 16 g (66.9 mmol) of 3-hydroxy-2,4,6-trichlorobenzamide is suspended in 100 ml of methanol and dissolved by adding 1.54 g (66.9 mmol) of sodium. After adding 14 g (73 mmol) of the ethyl ester of 4-bromobutyric acid, the mixture is maintained under reflux for 70 hours; then the solution is concentrated to dryness and the residue extracted by boiling with ether. After several hours of stirring in an ice bath, the crystallized product is vacuum-filtered, washed with ice-cold ether, and dried at room temperature, yielding 13.4 g (59% of theory) of the methyl ester of 4-(3-carbamoyl-2,4,6-trichlorophenoxy)butyric acid as a white powder, mp 117°–118' C. The compound is thereafter suspended in 150 ml of water and, after adding 8 ml of concentrated sodium hydroxide solution, saponified within 3 hours at 60° C. The solution is filtered over active carbon and brought to pH 2 by adding concentrated hydrochloric acid. After several hours of stirring in an ice bath, the precipitate is vacuum-filtered, washed with water, and dried at 50° C., thus producing 11.4 g (89% of theory) of 4-(3-carbamoyl-2,4,6-trichlorophenoxy)butyric acid as a white powder, mp 165°–166° C.

EXAMPLE 13

3-Carbamoyl-2,4,6-triiodophenoxyacetic Acid 0.436 g (19 mmol) of sodium is dissolved in 20 ml of ethanol. Then 9.78 g (19 mmol) of 3-hydroxy-2,4,6-triiodobenzamide and subsequently 3.5 g (21 mmol) of ethyl bromoacetate are added thereto. The mixture is heated for one hour to reflux and, after several hours of stirring in an ice bath, the resultant 3-carbamoyl-2,4,6-triiodophenoxyacetic acid ethyl ester is vacuum-filtered, washed with a small amount of ice-cold ethanol, and suspended in 80 ml of water. The mixture is brought to pH 12 by adding concentrated sodium hydroxide solution, stirred for 30 minutes at $\alpha°$ C., the solution is treated with 1 g of active carbon, filtered, and brought to pH 1 by the dropwise addition of dilute hydrochloric acid. After several hours of stirring in an ice bath, the thus-formed precipitate is vacuum-filtered, washed with water, and dried, thus obtaining 10.2 g (89% of theory) of 3-carbamoyl-2,4,6-triiodophenoxyacetic acid as a white powder, mp 211°–213° C. (decomposition).

EXAMPLE 14

3-Carbamoyl-2,4,6-triiodophenoxyacetic Acid 27.3 g (49 mmol) of 3-cyano-2,4,6-triiodophenoxyacetic acid is stirred in 100 ml of 2N sodium hydroxide solution for 3 hours at 50° C. The resultant alkaline solution is filtered over active carbon for purifying and decolorizing and then brought to pH 2 by adding 2N hydrochloric acid. After several hours of stirring in an ice bath, the yield is 23.9 g (85% of theory) of 3-carbamoyl-2,4,6-triiodophenoxyacetic acid as a white powder, mp 211°–213° C. (decomposition).

EXAMPLE 15

Preparation of Sweetener Tablets:

10 kg of 3-carbamoyl-2,4,6-triiodophenoxyacetic acid sodium salt, 40.75 kg of fructose, and 0.25 kg of polyoxyethylene-polyoxypropylene polymer, molecular weight 6800 ("Pluronic" F 68) are mixed together, and the mixture is processed into 50 mg tablets. Accordingly, one tablet contains 10 mg of 3-carbamoyl-2,4,6-triiodophenoxyacetic acid, 40.75 mg of fructose, and 0.25 mg of "Pluronic" F68.

EXAMPLE 16

Preparation of Sweetener Solution:

15 g of 3-carbamoyl-2,4,6-triiodophenoxyacetic acid sodium salt and 3 g of gelatin are dissolved in 250 ml of distilled water; the clear solution is replenished to 1000 mol with distillated water, and then the solution is dispensed into dropper bottles.

EXAMPLE 17

3-carbamoyl-2,4,6-trichlorophenoxyacetic acid 29.4 g (0.1 mol) of 3-cyano-2,4,6-trichlorophenoxyacetic acid methyl ester are suspended in 300 ml of water. After addition of 35 ml of concentrated sodium hydroxide, the reaction mixture is heated at 60° C. until a clear solution is obtained. After filtration over active carbon, the solution is cooled and brought to pH 2 by dropwise addition of 50% concentrated hydrochloric acid. The mixture is stirred for 2 hours in an ice bath, after which the resultant precipitate is vacuum-filtered, washed with water and dried t 50° C., thus producing 25.4 g (85% of theory) of 3-carbamoyl-2,4,6-trichlorophenoxyacetic acid as a white powder, mp 261°–262° C.

EXAMPLE 18

3-(3carbamoyl-2,4,6-tribromophenyl)-2-methoxypropionic acid 50 g (223 mmol) of 3-(3-nitrophenyl)-2-methoxyacrylic acid is suspended in 785 ml of water and brought into solution by the addition of 30 ml of concentrated ammonia. After addition of 3 g of Raney nickel, the mixture is hydrogenated at 80 bar until uptake of hydrogen ceases. The solution is filtered, 325 g of salt are added, and the resultant solution is thoroughly extracted with tetrahydrofuran. The combined tetrahydrofuran extracts are dried over sodium sulfate, filtered over active carbon and concentrated, thus producing 38.6 g (88% of theory) of 3-(3-aminophenyl)-2-methoxypropionic acid. This product is dissolved in 1 liter of water by the addition of 110 ml of 2N ammonia. The resultant solution is treated first with 160 ml of glacial acetic acid, and then with 36 ml of bromine in 160 ml of glacial acetic acid added dropwise at room temperature over the course of 2 hours. The reaction mixture is stirred for several hours in an ice bath, the resultant precipitate is vacuum-filtered, washed with water and dried at 50° C., thus producing 66 g (73% of theory) of 3-(3-amino-2,4,6-tribromophenyl)-2-methoxypropionic acid, as a white powder, mp 173°–175° C. 32 g (74 mmol) of this compound is added portionwise at +5° C. at 80 ml of nitrosylsulfuric acid. Then, 40 ml of glacial acetic acid is added, and the mixture is stirred for 2 hours at +5° C. The mixture is poured onto 360 g of ice, and the resultant mixture is added to a solution of 33 g of copper (I) cyanide, 62 g of potassium cyanide and 464 ml of concentrated ammonia in 297 ml of water, resulting in discharge of gas. The reaction mixture is stirred overnight at room temperature, treated with 1 liter of ethyl acetate, and brought to pH 2 by addition of concentrated hydrochloric acid. After pressure filtration, the ethyl acetate phase is separated and the aqueous phase is again throroughly extracted with ehtyl acetate. The combined ethyl acetate extracts are dried over sodium sulfate, filtered over active carbon and vacuum-concentrated to dryness, thus producing 24 g of crude 3-(3-cyano-2,4,6-tribromphenyl)-2-methoxypropionic acid. This product is hydrolyzed to the amide by stirring at 60° C. in 100 ml of water containing 3 g of caustic soda for 3 hours. The resultant solution is filtered over active carbon and the filtrate is brought to pH 2 with concentrated hydrochloric acid. The resultant mixture containing a precipitate is stirred for several hours in an ice bath, vacuum-filtered, washed with water and dried at 50° C., thus producing 27.5 g (81% of theory) of 3-(3- carbamoyl-2,4,6-tribromophenyl)2-methoxypropionic acid, as a white powder, mp 138°–139° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sweetener, comprising an effective sweetening amount of a compound having the formula I

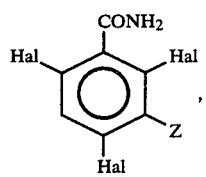

wherein
Hal is iodine; and
Z is a carboxyl group or the group

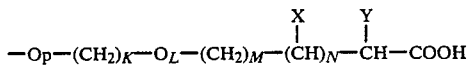

wherein
P is 1 and L is 0 or 1, with the proviso that L is 0 when K is 0;
K is 0, 2, 3 or 4;
M is 0, 1, 2 or 3;
N is 0 or 1;
X is a hydrogen atom;
Y is a hydrogen atom or a lower alkyl group of 1–4 carbon atoms, or when either M or N is other than 0, a hydroxy group, a $C_{1-6}$ group or a $C_{1-4}$ acyloxy group, or when N is 1 and M is other than 0, X and Y together represent an additional carbon-carbon bond; or
P and L are each 0;
K is 0, 2, 3 or 4;
M is 0, 1, 2 or 3;
N is 0 or 1;
X is a hydrogen atom;
Y is a hydrogen atom, a lower alkyl group of 1–4 carbon atoms, a hydroxy group, a $C_{1-6}$ alkoxy group, a $C_{1-4}$ acyloxy group or, when N is 1, X and Y together represents an additional carbon-carbon bond; or a salt thereof with an inorganic base; and a non-toxic vehicle.

2. A sweetener according to claim 1, wherein in Formula I, Z is

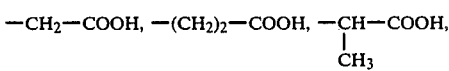

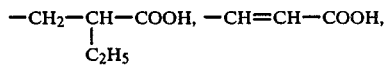

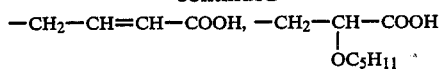

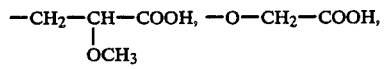

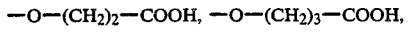

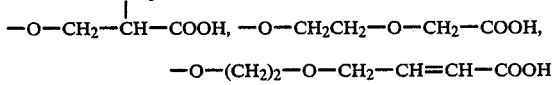

3. A sweetener according to claim 1, wherein in Formula I, Y is H, $OCH_3$, $OC_2H_5$, $O-nC_5H_{11}$, $CH_3$, $C_2H_5$, acetoxy or propanoyloxy.

4. A composition of claim 1, wherein Z is a carboxy group or the group

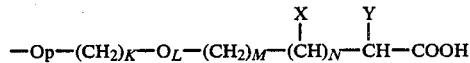

wherein
(1) P and L are each ;
K is 0, 2, 3 or 4;
M is 0, 1, 2 or 3;
N is 0 or 1;
X is a hydrogen atom;
Y is a hydrogen tom, a lower alkyl group of 1–4 carbon atoms, a hydroxy group, a $C_{1-6}$ alkoxy group or a $C_{1-4}$ acyloxy group, or when N is 1, X and Y together form an additional carbon bond; or
(2) P and L are each 1;
K is 2, 3 or 4;
M is 0, 1, 2 or 3;
N is 0 or 1;
X is a hydrogen atom; and
Y is a hydrogen atom or a lower alkyl group of 1–4 carbon atoms.

5. A composition of claim 1, wherein P and L are each 1.

6. A composition of claim 1, wherein X and Y together represent an additional carbon-carbon bond.

7. A composition of claim 1, wherein Y is hydroxy, alkoxy or acyloxy.

8. A method of reducing the intake of sugar in a diet of a human or an animal, comprising substituting for at least a portion of the sugar in said diet a sweetener according to claim 4.

9. A method of reducing the caloric content of a diet of a human or an animal, comprising substituting for at least a portion of the caloric sweetener in said diet a sweetener according to claim 4.

10. An ingestible composition, comprising as a sweetening agent an effective sweetening amount of a sweetener according to claim 4.

11. A method of reducing the intake of sugar in the diet of a human or an animal, comprising substituting for at least a portion of the sugar in said diet a sweetener according to claim 1.

12. A method of reducing the caloric content of the diet of a human or an animal, comprising substituting for at least a portion of the caloric sweeteners in said diet a sweetener according to claim 1.

13. An ingestible composition, comprising as a sweetening agent an effective sweetening amount of a sweetener according to claim 1.

* * * * *

UNITED STATES PATENT AND TRADEMARK OFFICE
CERTIFICATE OF CORRECTION

PATENT NO. : 4,869,913

DATED : September 26, 1989

INVENTOR(S) : GRIES ET AL

It is certified that error appears in the above-identified patent and that said Letters Patent is hereby corrected as shown below:

Title page, Foreign Application Priority Data:

reads "Dec. 11, 1980 [DE] Fed. Rep. of Germany ....... 3048918"

should read -- Dec. 22, 1980 [DE] Fed. Rep. of Germany ....... 3048918 --

Signed and Sealed this

Fourth Day of September, 1990

Attest:

HARRY F. MANBECK, JR.

*Attesting Officer*  *Commissioner of Patents and Trademarks*